(12) United States Patent
Sekido

(10) Patent No.: US 8,787,743 B2
(45) Date of Patent: Jul. 22, 2014

(54) CABLE CONNECTION STRUCTURE AND ENDOSCOPE APPARATUS

(71) Applicant: Olympus Corporation, Tokyo (JP)

(72) Inventor: Takanori Sekido, Machida (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 13/670,617

(22) Filed: Nov. 7, 2012

(65) Prior Publication Data

US 2013/0064530 A1    Mar. 14, 2013

Related U.S. Application Data

(63) Continuation of application No. PCT/JP2011/060668, filed on May 9, 2011.

(30) Foreign Application Priority Data

May 10, 2010    (JP) .................................. 2010-108673

(51) Int. Cl.
   *A61B 1/04* (2006.01)

(52) U.S. Cl.
   USPC ............................ 396/17; 600/110; 174/74 R

(58) Field of Classification Search
   USPC ............ 396/17; 174/60, 74 R, 75 R; 600/110
   See application file for complete search history.

(56) References Cited

U.S. PATENT DOCUMENTS

| 4,678,865 | A | * | 7/1987 | Sherwin | .......................... 174/36 |
| 5,879,285 | A | * | 3/1999 | Ishii | ............................. 600/110 |
| 2011/0115882 | A1 | * | 5/2011 | Shahinian et al. | .............. 348/45 |
| 2012/0103686 | A1 | * | 5/2012 | Sekido et al. | ............... 174/75 R |

FOREIGN PATENT DOCUMENTS

| JP | 05290640 | A | 11/1993 |
| JP | 09090237 | A | 4/1997 |
| JP | 11283696 | A | 10/1999 |
| JP | 2001-015187 | | 1/2001 |
| JP | 2005085625 | A | 3/2005 |
| JP | 3863583 | | 10/2006 |
| JP | 2007-234454 | | 9/2007 |
| JP | 2008176970 | A | 7/2008 |
| JP | 2010-056033 | | 3/2010 |

OTHER PUBLICATIONS

Abstract of Japanese Patent Publication No. JP 09-090237, dated Apr. 4, 1997 (corresponding to JP 3863583).
International Search Report dated Jun. 7, 2011 issued in PCT/JP2011/060668.
Japanese Office Action dated May 27, 2014 issued in corresponding Application No. 2010-108673 together with an English language translation.

* cited by examiner

*Primary Examiner* — Clayton E Laballe
*Assistant Examiner* — Warren K Fenwick
(74) *Attorney, Agent, or Firm* — Scully, Scott, Murphy & Presser, P.C.

(57) ABSTRACT

A cable connection structure includes: a cable including a core wire and an external covering layer covering the core wire; a board on which an electrode is formed, the core wire being electrically connected to the electrode at an end face of the cable; and a compressing member attached to an outer periphery of the cable and radially compressing a part in a longitudinal direction of the cable.

19 Claims, 8 Drawing Sheets

CABLE CONNECTION STRUCTURE AND ENDOSCOPE APPARATUS

CROSS-REFERENCE TO RELATED APPLICATIONS

This application is a continuation of PCT international application Ser. No. PCT/JP2011/060668 filed on May 9, 2011 which designates the United States, incorporated herein by reference, and which claims the benefit of priority from Japanese Patent Application No. 2010-108673, filed on May 10, 2010, incorporated herein by reference.

BACKGROUND OF THE INVENTION

1. Field of the Invention

The present invention relates to a cable connection structure that connects a cable to a board, and an endoscope apparatus using the cable connection structure.

2. Description of the Related Art

In recent years, medical and industrial endoscopes have been widely used. Some medical endoscopes include, for example, an imaging device with a built-in imaging element such as a CCD provided at a distal end of an insertion portion to be inserted into the body. A lesion can be observed by inserting the insertion portion deep into the body. Furthermore, appropriate use of a treatment tool in combination enables examination and treatment of the inside of the body.

To display an image on a monitor, such an endoscope converts image information, captured by the imaging element, into electrical signals and transmits the signals to a signal processing device through a signal line. The transmitted signals are then processed in the signal processing device. For this purpose and in order to, for example, transmit image signals and clock signals and to supply driving power to the imaging element provided in the endoscope, the imaging element and the signal processing device are connected through a cable assembly including a plurality of cables put together.

Concerning the connection of the cable assembly, Japanese Patent No. 3863583 discloses a technology for collectively connecting the cable assembly, which includes a plurality of coaxial cables, to a circuit board provided with electrodes. With this technology, first, a distal end portion of each coaxial cable is fixed by an aligning block, and a distal end face of an electrical wire of each coaxial cable and a distal end face of the aligning block are ground to match each other. After that, the distal end faces of the electrical wires and the circuit board provided with electrodes are made to face each other, and then connected to each other via an anisotropic conductive sheet or connection bumps, for example. Furthermore, for reinforcement, the periphery of the connection portion is coated with an epoxy-based adhesive, which is then solidified.

SUMMARY OF THE INVENTION

A cable connection structure according to an aspect of the present invention includes: a cable including a core wire and an external covering layer covering the core wire; a board on which an electrode is formed, the core wire being electrically connected to the electrode at an end face of the cable; and a compressing member attached to an outer periphery of the cable and radially compressing a part in a longitudinal direction of the cable.

A cable connection structure according to another aspect of the present invention includes: a plurality of cables aligned to be in contact with each other at a part of an outer periphery thereof, each cable including a core wire and an external covering layer covering the core wire; a board on which a plurality of electrodes is formed, the core wires being electrically connected to the electrodes at end faces of the plurality of cables; and a compressing member attached to outer peripheries of the plurality of cables and radially compressing a part in a longitudinal direction of the plurality of cables.

The above and other features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Cable connection structures according to embodiments of the present invention will be described below in detail with reference to the drawings. Note that the present invention is by no means limited by the embodiments.

First Embodiment

Figure 1:
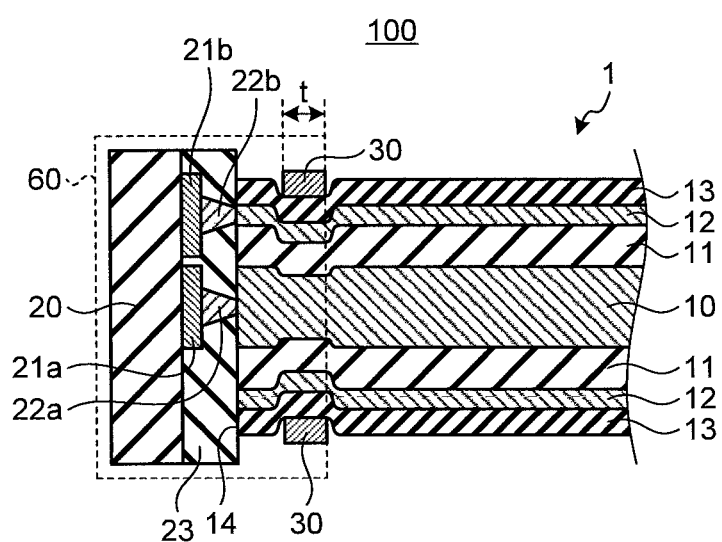
FIG. 1 is a cross-sectional view illustrating a cable connection structure according to a first embodiment of the present invention.

FIG. 1 is a cross-sectional view illustrating a cable connection structure according to a first embodiment of the present invention. A cable connection structure 100 illustrated in FIG.

1 includes a coaxial cable 1, a board 20, and a swaging member 30 as a compressing member. The board 20 is connected to an end face of the coaxial cable 1 via electrodes 21a and 21b. The swaging member 30 is attached to the periphery of the coaxial cable 1 and compresses a part of the coaxial cable 1 radially.

The coaxial cable 1 has a structure in which a core wire 10, an internal insulating layer 11, a shield layer (external conductive layer) 12, and a jacket layer (external covering layer) 13 are arranged concentrically. The core wire 10 is formed of a conductor. The internal insulating layer 11 is arranged around the core wire 10 and formed of an insulator. The shield layer 12 is arranged around the internal insulating layer 11 and formed of a conductor. The jacket layer 13 is arranged around the shield layer 12 and formed of an insulator.

The board 20 is a circuit board on which various devices such as an imaging element are arranged. The electrode 21a electrically connected to the devices is formed on a main surface of the board 20 at a position facing the core wire 10. The electrode 21b is formed on the main surface at a position facing the shield layer 12.

The coaxial cable 1 and the board 20 configured as described above are electrically connected via connection bumps 22a and 22b formed of solder or gold (Au), for example, at a connection end face 14 of the coaxial cable 1. In addition, a reinforcing resin 23 such as an epoxy resin is filled between the connection end face 14 and the board 20, further securing the connection therebetween.

The swaging member 30 may have any shape such as a C-shape, a saddle-shape, or an O-shape (ring-shape) as long as it can apply a compressive force to the coaxial cable 1 externally. The cross-section of the swaging member 30 may have various shapes, such as a rectangle as illustrated in FIG. 1, a trapezoid, a triangle, a semicircle, or a semiellipse. For example, in the case where the thickness t of the swaging member 30 used (the length thereof in the direction parallel to the longitudinal direction of the coaxial cable 1 when attached thereto) is smaller at the inner periphery than at the outer periphery thereof (e.g., the cross-section has a trapezoidal shape), it is easy to press the swaging member into the coaxial cable 1, and the concentration of the compressive force makes it possible to obtain a higher compression effect.

The swaging member 30 may be attached to any position on the coaxial cable 1, but is preferably attached near the connection portion between the coaxial cable 1 and the board 20. This is for avoiding the generation of a tensile load on the core wire 10 between the connection portion and the swaging member 30. Furthermore, the swaging member 30 is preferably arranged nearer the connection portion, but not to the extent of deforming (bending) the coaxial cable 1 between the connection portion and the swaging member 30.

The function of the swaging member 30 in the first embodiment will be described next. By compressing the coaxial cable 1, the swaging member 30 presses the jacket layer 13, the shield layer 12, and the internal insulating layer 11 toward the core wire 10. As a result, at this compressed portion, the movement of the core wire 10 relative to the other layers (the internal insulating layer 11 to the jacket layer 13) is suppressed. Therefore, even when a tensile load acts on the core wire 10 due to the coaxial cable 1 being deformed or processed at a position distant from the swaging member 30, the compressed portion of the coaxial cable 1 shuts off the transmission of the tensile load. That is, the tensile load of pulling the core wire 10 away from the connection bump 22a is not transmitted to a portion near the board 20 beyond the compressed portion. It is thus possible to securely maintain the connection between the core wire 10 and the electrode 21a.

Figure 2A:
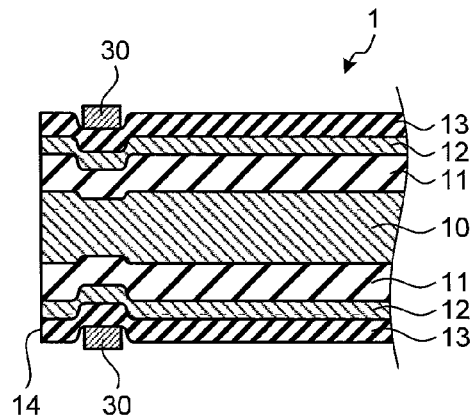
FIG. 2A is a cross-sectional view illustrating a swaging member attached to a coaxial cable.

Next, a method of forming the cable connection structure illustrated in FIG. 1 will be described with reference to FIGS. 2A to 2C. First, as illustrated in FIG. 2A, the swaging member 30 is attached to the surface of the coaxial cable 1 (the outer periphery of the jacket layer 13). The swaging member 30 is then swaged using, for example, a swaging tool to be fixed while applying a compressive force to the coaxial cable 1 radially. After that, an end of the coaxial cable 1 is subjected to a grinding process or the like to thereby expose the core wire 10 to the jacket layer 13 on the same plane. To improve the connection efficiency of the core wire 10 and the shield layer 12, concentric conductive films may be formed, by plating or sputtering, for example, on the end faces of the core wire 10 and the shield layer 12, which have been exposed on this plane (connection end face 14).

Figure 2B:
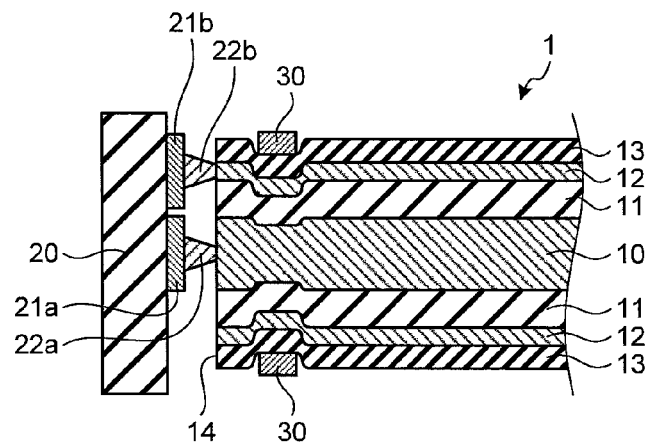
FIG. 2B is a cross-sectional view illustrating the coaxial cable connected to electrodes on a board.
Figure 2C:
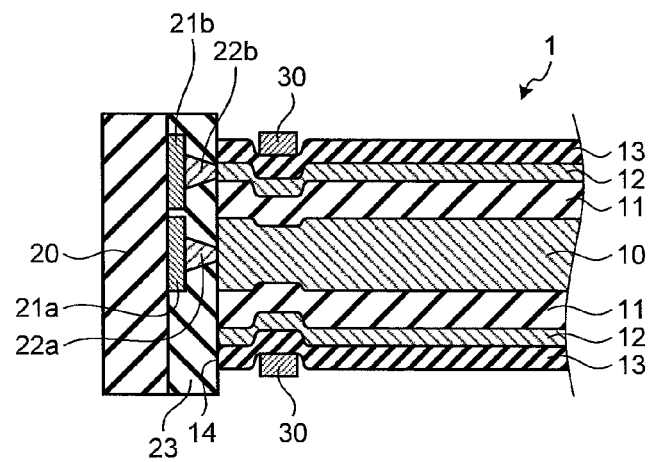
FIG. 2C is a cross-sectional view illustrating the filling of a reinforcing resin.

Next, as illustrated in FIG. 2B, the core wire 10 and the shield layer 12 are connected to the electrodes 21a and 21b via the connection bumps 22a and 22b, respectively. Furthermore, as illustrated in FIG. 2C, the reinforcing resin 23 is filled between the connection end face 14 and the board 20 to reinforce the connection between the coaxial cable 1 and the board 20. In this manner, the cable connection structure 100 illustrated in FIG. 1 is formed.

Second Embodiment

Figure 3:
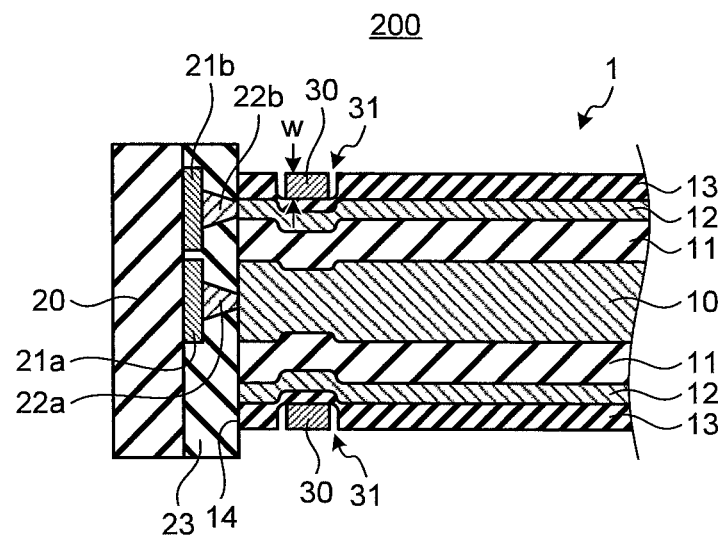
FIG. 3 is a cross-sectional view illustrating a cable connection structure according to a second embodiment of the present invention.

A cable connection structure according to a second embodiment of the present invention will be described next. FIG. 3 is a cross-sectional view illustrating the cable connection structure according to the second embodiment.

A cable connection structure 200 illustrated in FIG. 3 has a groove 31 formed by partially removing a jacket layer 13 in the thickness direction thereof. A swaging member 30 is arranged in the groove 31 to compress a coaxial cable 1. With this configuration, the swaging member 30 is arranged so as not to protrude from the surface of the jacket layer 13. The other configuration is similar to that illustrated in FIG. 1.

The depth of the groove 31 is set at least equal to or larger than the width w of the swaging member 30 (the length thereof in the radial direction of the coaxial cable 1 when attached thereto), with the coaxial cable 1 compressed by the swaging member 30. With the depth of the groove 31 formed being equal to or larger than the width w of the swaging member 30, it is possible to reliably prevent the protrusion of the swaging member 30 by arranging, in the groove 31, and then swaging the swaging member 30, which is more preferable. Note that the groove 31 can be formed by a cutting tool or through laser processing, for example.

According to the second embodiment as described above, it is possible to suppress the increase in diameter in the vicinity of the swaging member 30 while securely maintaining the connection between the core wire 10 of the coaxial cable 1 and the electrode 21a, by compressing the coaxial cable 1 with the swaging member 30.

Third Embodiment

Figure 4:
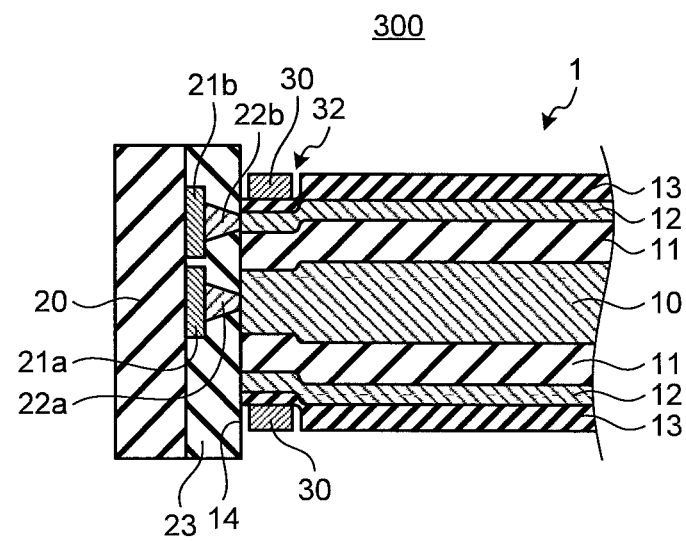
FIG. 4 is a cross-sectional view illustrating a cable connection structure according to a third embodiment of the present invention.

A cable connection structure according to a third embodiment of the present invention will be described next. FIG. 4 is a cross-sectional view illustrating the cable connection structure according to the third embodiment.

In a cable connection structure 300 illustrated in FIG. 4, a swaging member 30 is arranged in the vicinity of a connection end face 14 of a coaxial cable 1. The other configuration is similar to that illustrated in FIG. 1.

As described above, if the swaging member 30 is attached to a position distant from the connection portion between the coaxial cable 1 and the board 20, the coaxial cable 1 may be deformed, for example, between the connection portion and the swaging member 30, and the tensile load acting on the core wire 10 may be transmitted to the connection portion. In the third embodiment, therefore, the swaging member 30 is arranged in the vicinity of the connection end face 14 of the coaxial cable 1, preferably such that the end face of the swaging member 30 on the side of the board would match the connection end face 14. This configuration prevents the generation of a tensile load between the swaging member 30 and the connection end face 14 and further securely maintains the connection between the core wire 10 of the coaxial cable 1 and an electrode 21a.

Although the swaging member 30 is arranged in a groove 32 formed in a jacket layer 13 in FIG. 4, the swaging member 30 may alternatively be arranged on the surface of the jacket layer 13.

A method of forming the cable connection structure 300 illustrated in FIG. 4 will be described here.

Figure 5A:
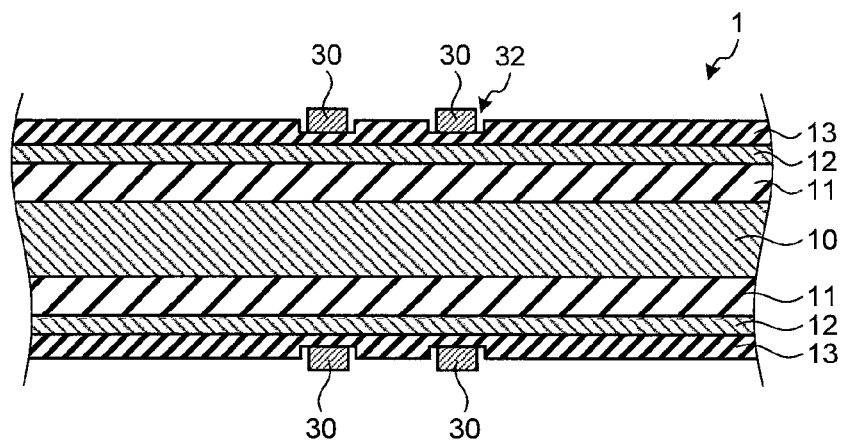
FIG. 5A is a cross-sectional view illustrating swaging members fitted into grooves formed in the coaxial cable.

First, as illustrated in FIG. 5A, the grooves 32 are formed by a cutting tool or through laser processing, for example, at two positions on the jacket layer 13 of the coaxial cable 1.

Figure 5B:
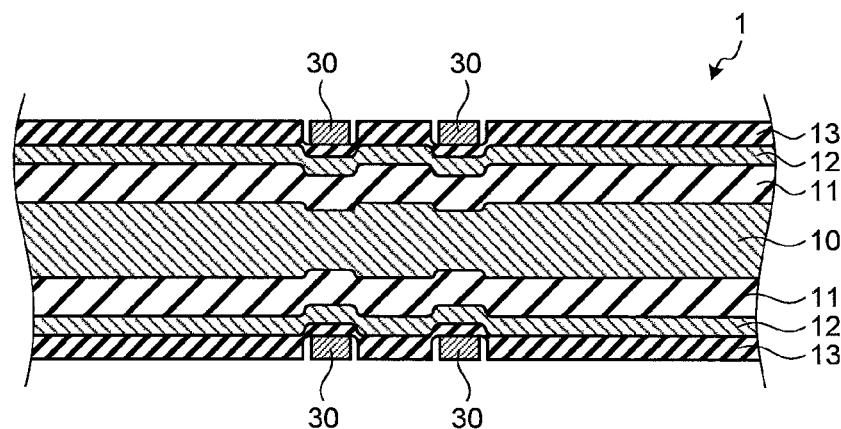
FIG. 5B is a cross-sectional view illustrating the coaxial cable swaged by the swaging members.
Figure 5C:
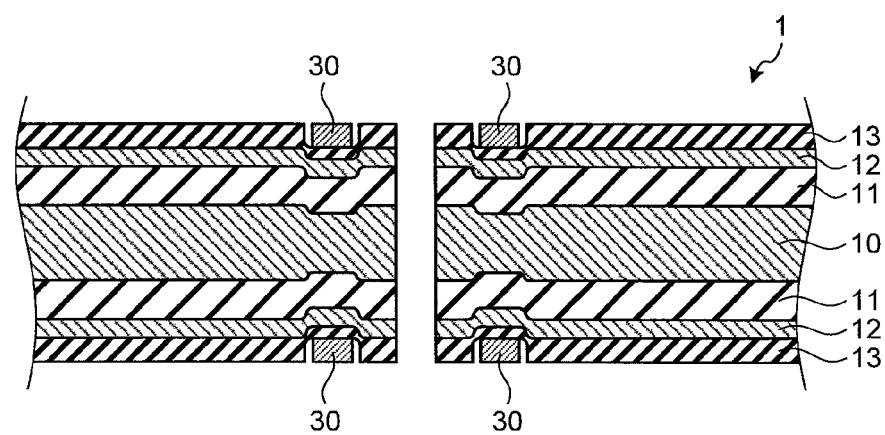
FIG. 5C is a cross-sectional view illustrating the swaged coaxial cable that has been cut off.
Figure 5D:
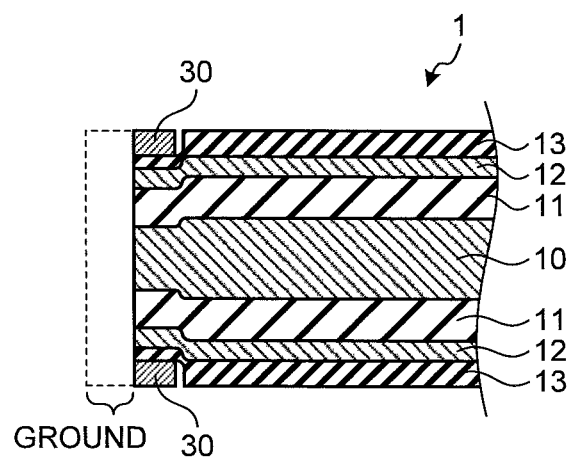
FIG. 5D is a cross-sectional view illustrating the coaxial cable ground up to the vicinity of the swaging member.

Then, the swaging members 30 are respectively arranged in the grooves 32 and swaged using a swaging tool, for example, whereby the swaging members 30 are fixed to the coaxial cable 1 as illustrated in FIG. 5B. Next, as illustrated in FIG. 5C, a portion between the swaging members 30 arranged at the two positions is cut off by a cutting tool or through laser processing, for example. After that, as illustrated in FIG. 5D, the cut surface of the coaxial cable 1 is ground up to the vicinity of the swaging member 30, preferably up to the end face of the swaging member 30. As a result, the core wire 10 to the jacket layer 13 are exposed on the same plane. In the drawing, the cut surface has been ground up to the end face of the swaging member 30. To improve the connection efficiency of the core wire 10 and the shield layer 12, concentric conductive films may be formed, by plating or sputtering, for example, on the end faces of the core wire 10 and the shield layer 12.

Figure 5E:
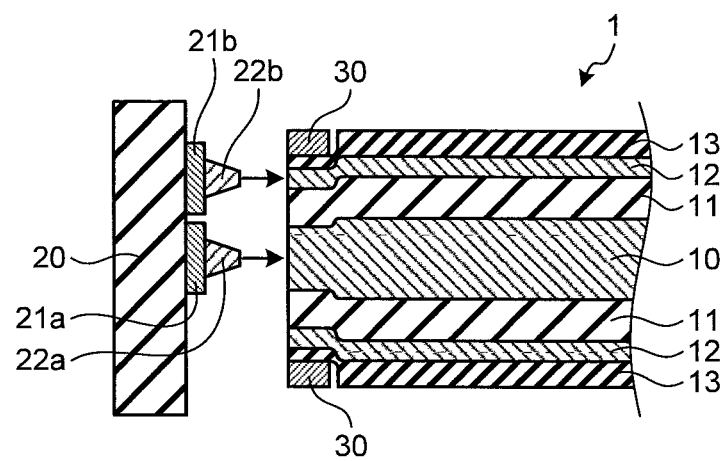
FIG. 5E is a cross-sectional view illustrating the swaged coaxial cable being positioned relative to electrodes on a board.

Next, as illustrated in FIG. 5E, the end face of the coaxial cable 1 and the board 20 on which the electrodes 21a and 21b have been provided are made to face each other and positioned relative to each other. In this case, the positions of the electrodes 21a and 21b are determined in advance so as to match the positions of the core wire 10 and the shield layer 12, respectively, with the coaxial cable 1 swaged. The core wire 10 and the shield layer 12 are then connected to the electrodes 21a and 21b via connection bumps 22a and 22b, respectively. Furthermore, a reinforcing resin 23 is filled between the end face of the coaxial cable 1 and the board 20 to reinforce the connection between the coaxial cable 1 and the board 20, whereby the cable connection structure 300 illustrated in FIG. 4 is formed.

Note that, in the description above, the swaging members 30 are attached to the two positions on the coaxial cable 1 in order to easily cut off the coaxial cable 1 with an even load applied to each of both sides of the cut portion. Alternatively, the swaging member 1 may be attached only to one position, and the coaxial cable 1 may be cut off in the vicinity of that position.

Fourth Embodiment

Figure 6:
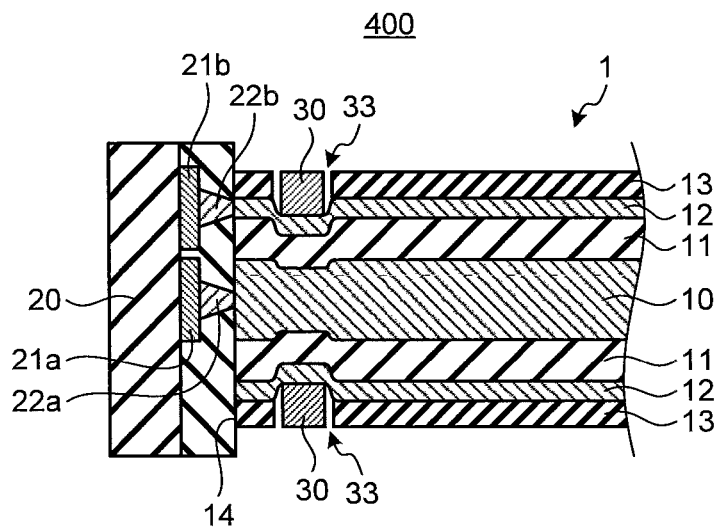
FIG. 6 is a cross-sectional view illustrating a cable connection structure according to a fourth embodiment of the present invention.

A cable connection structure according to a fourth embodiment of the present invention will be described next. FIG. 6 is a cross-sectional view illustrating the cable connection structure according to the fourth embodiment.

A cable connection structure 400 illustrated in FIG. 6 has a groove 33 formed by removing a jacket layer 13 of a coaxial cable 1. A swaging member 30 is arranged in the groove 33 to compress the coaxial cable 1. The other configuration is similar to that illustrated in FIG. 1.

In this manner, by entirely removing the jacket layer 13 at the portion compressed by the swaging member 30, the number of layers interposed between the swaging member 30 and a core wire 10 is reduced. Therefore, the compressive force applied by the swaging member 30 is more easily transmitted to the core wire 10. This makes it possible to further reliably suppress the movement of the core wire 10 relative to the other layers, and thus to further securely maintain the connection between the core wire 10 and an electrode 21a.

In this case, if the swaging member 30 is formed of an insulating material, the swaging member 30, instead of the removed jacket layer 13, can protect a shield layer 12.

As a modification of the fourth embodiment, the groove 33 may be formed in the vicinity of a connection end face 14 in the same manner as the third embodiment, and the end face of the swaging member 30 may be made to substantially match the connection end face 14. In this case, if the swaging member 30 is formed of a conductive material, the swaging member 30 can serve as the connection end face of the shield layer 12. This makes it easy to position the shield layer 12 and an electrode 21b relative to each other.

Furthermore, in this case, the outer peripheral surface of the swaging member 30 may be covered with an insulating material. As a result, the swaging member 30 can serve as a protective member for, and the connection end face of, the shield layer 12.

Fifth Embodiment

Figure 7:
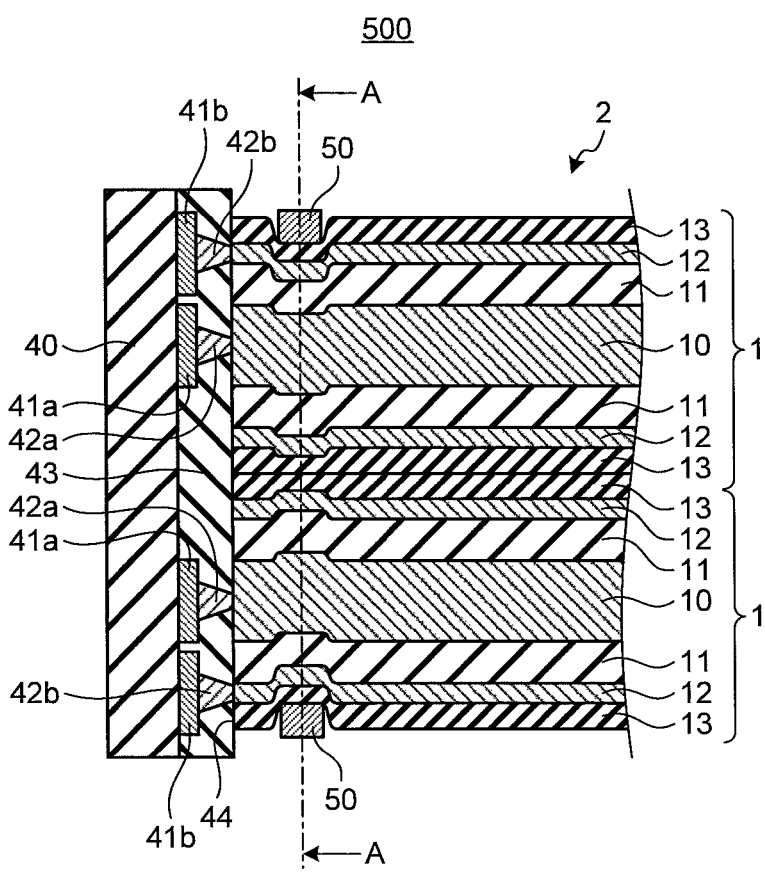
FIG. 7 is a cross-sectional view illustrating a cable connection structure according to a fifth embodiment of the present invention.

A cable connection structure according to a fifth embodiment of the present invention will be described next. FIG. 7 is a cross-sectional view illustrating the cable connection structure according to the fifth embodiment.

A cable connection structure 500 illustrated in FIG. 7 includes a cable assembly 2, a board 40, and a swaging member 50. The cable assembly 2 includes a plurality of coaxial cables 1 aligned to be in contact with each other at a part of the outer periphery thereof. The board 40 is connected to an end face of the cable assembly 2 via electrodes 41a and 41b. The swaging member 50 is attached to the cable assembly 2 and radially compresses a part thereof.

The board 40 is a circuit board on which various devices such as an imaging element are arranged. The electrode 41a electrically connected to the devices is formed on a main surface of the board 40 at a position facing a core wire 10 of each coaxial cable 1. The electrode 41b is formed on the main surface at a position facing a shield layer 12 of each coaxial cable 1. Each core wire 10 is electrically connected to the corresponding electrode 41a via a connection bump 42a, and each shield layer 12 is electrically connected to the corresponding electrode 41b via a connection bump 42b. Note that the connection bumps 42a and 42b are formed of solder or gold (Au), for example. In addition, a reinforcing resin 43 such as an epoxy resin is filled between an end face 44 of the cable assembly 2 and the board 40.

As in the present fifth embodiment, a single swaging member 50 may collectively compress the cable assembly 2 including the plurality of coaxial cables 1 put together. With this configuration, it is possible to suppress the movement of the core wire 10 relative to the other layers in each coaxial cable 1. Even when a tensile load acts on the core wire 10, therefore, the portion compressed by the swaging member 50 can shut off the transmission of the tensile load.

Figure 8A:
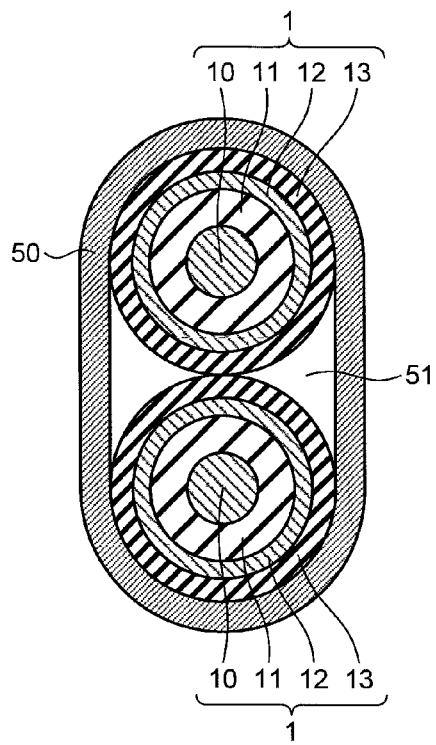
FIG. 8A is a cross-sectional view illustrating a cable assembly before being swaged and a swaging member.
Figure 8B:
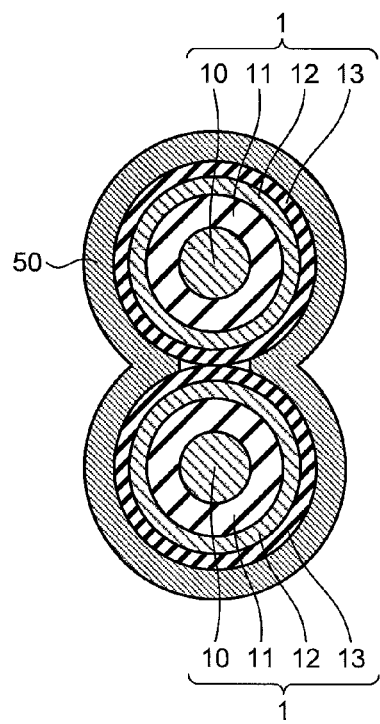
FIG. 8B is a cross-sectional view illustrating the swaged cable assembly and the swaging member.

The cable connection structure 500 configured as described above is formed as follows. That is, as illustrated in FIG. 8A, the plurality of coaxial cables 1 is put together, around which the swaging member 50 is arranged. The swaging member 50 is then swaged using, for example, a swaging tool by applying a load toward spaces 51 generated in the vicinity of the contact portion between the cables. As a result, as illustrated in FIG. 8B, the swaging member 50 is deformed along the outer peripheries of the coaxial cables 1, and fixed with the deformed portions fitted into the spaces 51.

The reason why the load is applied as described above to swage the swaging member 50 is as follows. The position and direction of applying the load to the swaging member 50 are not limited to those described above. The load may be applied in various directions, such as the vertical or horizontal direction in FIG. 8A. Regardless of the direction, however, the application of the load deforms the swaging member 50, increasing the dimensions thereof by the amount of deformation. However, with the load applied toward the spaces 51, the deformed portions of the swaging member 50 are fitted into the spaces 51, making it possible to suppress the increase in dimensions of the swaging member 50 at an area where the swaging member 50 is attached. In addition, with the swaging member 50 fitted into the spaces 51, each coaxial cable 1 receives the compressive force through a wide outer periphery thereof except the contact portion between the cables. It is thus possible to effectively suppress the movement of the core wire 10 relative to the other layers.

Note that in the fifth embodiment, the swaging member 50 is arranged on the surface of a jacket layer 13. Alternatively, as in the second or fourth embodiment, the swaging member 50 may be arranged in a groove formed in the jacket layer 13 to collectively compress the plurality of coaxial cables 1. Further alternatively, as in the third embodiment, the swaging member 50 may be arranged in the vicinity of the end face 44 of the cable assembly 2.

Although the swaging member is used as the compressing member in the first to fifth embodiments described above, any member capable of compressing the coaxial cable may be used. Examples of such a member include a tube clip, a crimping sleeve, and a splice.

Although the swaging member is attached only to one position on the coaxial cable 1 in the first to fifth embodiments, the swaging members may alternatively be arranged at a plurality of positions. For example, by arranging a plurality of swaging members at some intervals on a single coaxial cable 1 or a bunch of coaxial cables 1, it is possible to more reliably shut off the transmission of the tensile load to the core wire 10.

In the first to fifth embodiments, the core wire 10 and the shield layer 12 of the coaxial cable 1 are respectively connected to the electrodes 21a and 21b or the electrodes 41a and 41b via the bumps. Alternatively, for example, they may be electrically connected to each other using an anisotropic conductive material such as an ACP (anisotropic conductive paste) or an ACF (anisotropic conductive film).

Furthermore, although the connection structure for connecting the coaxial cable and the board has been described above, the type of the cable to be connected is not limited to the coaxial cable. The present invention is also applicable to, for example, a single-wire cable used for supplying power, a multicore cable including a plurality of core wires, and a cable assembly including a plurality of single-wire cables put together.

The first to fifth embodiments described above are applicable to, for example, an endoscope apparatus including an imaging module at a distal end of a cable. An example will be described below in which the cable connection structure 100 illustrated in FIG. 1 is applied to a medical endoscope apparatus to be introduced into a subject to capture the inside of a body cavity.

Figure 9:
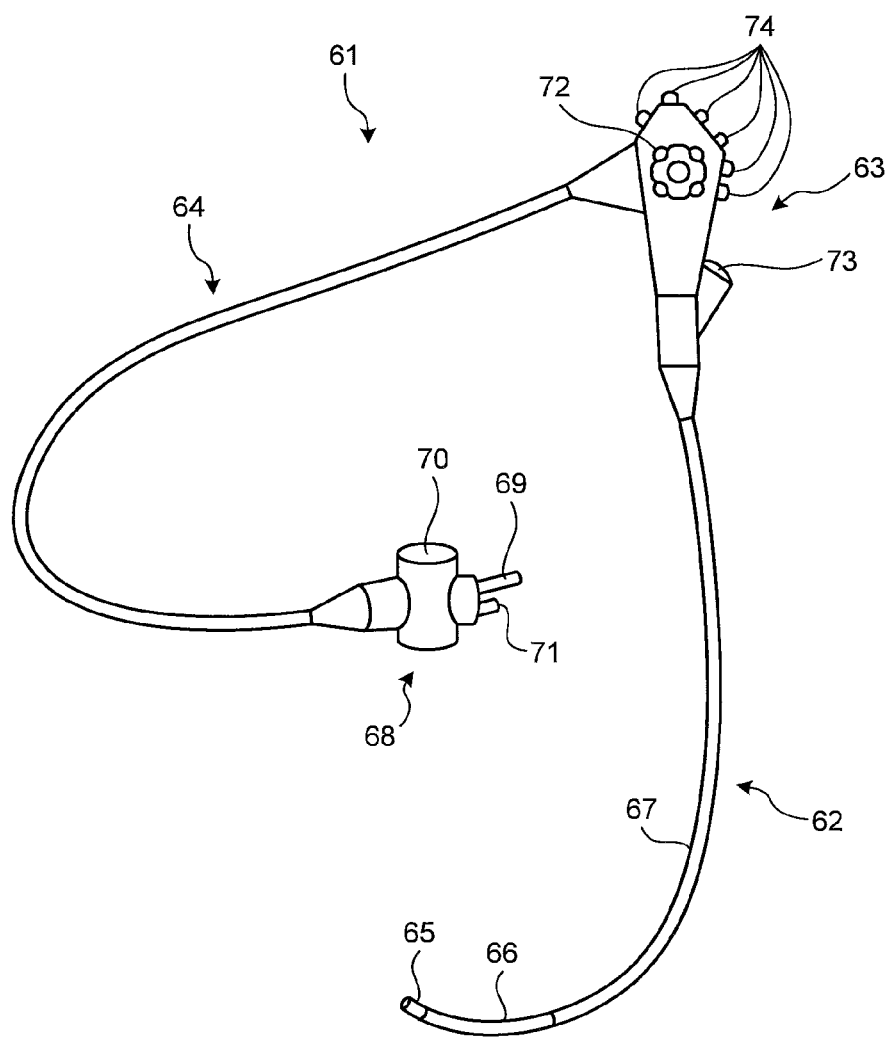
FIG. 9 is a schematic view illustrating the schematic configuration of an endoscope apparatus.

FIG. 9 is a view illustrating the schematic configuration of an endoscope apparatus. An endoscope apparatus 61 includes an elongated insertion portion 62, an operating unit 63, and a flexible universal cord 64. The operating unit 63 is at a proximal end of the insertion portion 62 and gripped by an operator of the endoscope apparatus. The universal cord 64 extends from a side portion of the operating unit 63. The universal cord 64 includes therein a light guide cable and an electrical cable, for example.

The insertion portion 62 includes a distal-end hard portion 65 and a flexible housing portion. The distal-end hard portion 65 includes a built-in imaging module having an imaging element such as a CCD. The housing portion houses therein cables connected to the imaging module, for example. The housing portion includes a bendable curved portion 66 and an elongated flexible tube portion 67. The curved portion 66 includes a plurality of bending portions. The flexible tube portion 67 is provided at a proximal end of the curved portion 66.

A connector portion 68 is provided at a leading end of the universal cord 64. The connector portion 68 includes a light guide connector 69, an electrical contact portion 70, and a blower tube 71, for example. The light guide connector 69 is detachably connected to a light source device. Electrical signals of a subject image obtained by photoelectric conversion using a CCD or the like are transmitted to a signal processing device or a control device through the electrical contact portion 70. Air is blown into a nozzle of the distal-end hard portion 65 through the blower tube 71. The light source device has a built-in halogen lamp, for example, and supplies light emitted from the halogen lamp, as illumination light, to the endoscope apparatus 61 connected to the light source device via the light guide connector 69. The signal processing device or the control device supplies power to the imaging element and receives electrical signals, obtained by photoelectric conversion, from the imaging element. The signal processing device or the control device processes the electrical signals captured by the imaging element, causes a display device, connected to the signal processing device or the control device, to display an image, and outputs drive signals for driving, and executing control such as gain adjustment of, the imaging element.

The operating unit 63 includes a bending knob 72, a treatment tool insertion portion 73, and a plurality of switches 74. The bending knob 72 is used for bending the curved portion 66 in the vertical or horizontal direction. A treatment tool such as a biopsy forceps or a laser probe is inserted into the body cavity through the treatment tool insertion portion 73. The plurality of switches 74 is used for operating peripheral equipment such as the signal processing device, the control device, and means for supplying air, water or gas. The endoscope apparatus 61, with a treatment tool inserted into an treatment tool insertion opening thereof, causes a distal-end treating portion of the treatment tool to protrude through a treatment tool insertion channel provided inside the endoscope apparatus, and performs, for example, biopsy by collecting lesional tissues using the biopsy forceps.

One end of the coaxial cable 1 illustrated in FIG. 1 is connected to an electrode of the switch 74 in the operating unit 63. The other end of the coaxial cable 1 reaches the distal-end hard portion 65 through the flexible tube portion 67 and the curved portion 66, and is connected to the electrode 21a formed on the board 20, on which the imaging element is arranged, by the cable connection structure 100 inside the distal-end hard portion 65. With the cable connection structure 100 applied in this manner, even when a tensile load acts on the core wire 10 of the coaxial cable 1 due to the deformation of the coaxial cable 1 housed in the flexible tube portion 67 and the curved portion 66, the swaging member 30 can shut off the transmission of the tensile load, making it possible to securely maintain the connection between the core wire 10 and the electrode 21a.

In this case, an end region 60 including at least the board 20 to the swaging member 30 is preferably housed in the distal-end hard portion 65. The distal-end hard portion 65 is not deformed, unlike the curved portion 66 or the flexible tube portion 67. With the end region 60 protected by the distal-end hard portion 65, therefore, it is possible to prevent the deformation of the coaxial cable 1 inside the end region 60 and to suppress the generation of the tensile load on the core wire 10. As a result, it is possible to more securely connect the core wire 10 and the electrode 21a.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A cable connection structure comprising:
   a cable including a core wire and an external covering layer covering the core wire;
   a board on which an electrode is formed, the core wire being electrically connected to the electrode at an end face of the cable; and
   a swaging member attached at a longitudinal position to at least a part of an outer periphery of the cable and radially compressing at least a portion of the cable at the longitudinal position.

2. The cable connection structure according to claim 1, wherein an outer diameter of the swaging member at the longitudinal position is equal to a diameter of the cable at a region without the swaging member attached.

3. The cable connection structure according to claim 1, wherein the swaging member is attached to a groove formed at the longitudinal position in the external covering layer.

4. The cable connection structure according to claim 1, wherein the longitudinal position is adjacent to an end face portion of the cable on the side of the board.

5. The cable connection structure according to claim 4, wherein the end face portion is formed by cutting the cable a predetermined distance from the swaging member.

6. The cable connection structure according to claim 5, wherein the end face portion is further formed by substantially removing the predetermined distance from the cable.

7. The cable connection structure according to claim 1, wherein the cable is a coaxial cable including:
   an internal insulating layer formed around the core wire; and
   an external conductive layer formed around the internal insulating layer and inside the external covering layer.

8. The cable connection structure according to claim 7, wherein the swaging member is attached to a region from which the external covering layer has been removed.

9. The cable connection structure according to claim 8, wherein the swaging member is formed of a conductive material.

10. The cable connection structure according to claim 9, wherein the swaging member includes a coating formed of an insulating material on an outer peripheral surface of the swaging member.

11. The cable connection structure according to claim 8, wherein the swaging member is formed of an insulating material.

12. An endoscope apparatus comprising:
    the cable connection structure according to claim 1; and
    an imaging element connected to the electrode formed on the board.

13. The endoscope apparatus according to claim 12, further comprising:
    a distal-end hard portion housing at least the imaging element, the board, and the swaging member; and
    a flexible housing portion housing the cable protruding from the distal-end hard portion.

14. The cable connection structure according to claim 1, wherein the end face portion of the cable includes a polished surface.

15. The cable connection structure according to claim 1, wherein an inner diameter of the swaging member at the longitudinal position is smaller than a diameter of the cable at a region without the swaging member attached.

16. A cable connection structure comprising:
    a plurality of cables aligned to be in contact with each other at a part of an outer periphery thereof, each cable including a core wire and an external covering layer covering the core wire;
    a board on which a plurality of electrodes is formed, the core wires being electrically connected to the electrodes at end faces of the plurality of cables; and
    a swaging member attached at a longitudinal position to at least a part of outer peripheries of the plurality of cables and radially compressing at least a portion of the plurality of cables at the longitudinal position.

17. The cable connection structure according to claim 16, wherein the swaging member is attached along the outer peripheries of the plurality of cables.

18. A cable connection structure comprising:
    a cable including at least a core wire and an external covering layer covering the core wire;
    a board on which an electrode is formed, the core wire being electrically connected to the electrode at an end face of the cable; and
    a compressing member attached to an outer periphery of the cable and radially compressing the external covering and at least the core wire of the cable.

19. The cable connection structure according to claim 18, wherein the compressing member is formed of a conductive material.

* * * * *